United States Patent
Bembenek et al.

[11] Patent Number: 6,135,770
[45] Date of Patent: Oct. 24, 2000

[54] CONTAINMENT CHAMBER FOR DENTAL ABRASION

[75] Inventors: John J. Bembenek, Burlington; Edmond L. Rampen, Oakville, both of Canada

[73] Assignee: Oral Health Innovations Ontario, Burlington, Canada

[21] Appl. No.: 09/394,336

[22] Filed: Sep. 13, 1999

[51] Int. Cl.[7] ..................................................... A61C 3/02
[52] U.S. Cl. ............................... 433/88; 433/136; 433/91
[58] Field of Search ............................... 433/88, 93, 140, 433/116, 136, 137, 138, 91

[56] References Cited

U.S. PATENT DOCUMENTS

| | | |
|---|---|---|
| 2,637,107 | 5/1953 | Daigle . |
| 3,478,432 | 11/1969 | Gross ...................................... 433/138 |
| 4,240,789 | 12/1980 | Rosenthaler ........................... 433/136 |
| 4,261,697 | 4/1981 | Newitter .................................. 433/137 |
| 4,889,490 | 12/1989 | Jenkinson . |
| 5,152,686 | 10/1992 | Duggan et al. ......................... 433/140 |
| 5,197,876 | 3/1993 | Coston . |
| 5,356,292 | 10/1994 | Ho . |
| 5,547,376 | 8/1996 | Harrel . |
| 6,024,566 | 2/2000 | Bruns et al. ............................ 433/136 |

OTHER PUBLICATIONS

Quintessence International, Aerosol Reduction During Air Polishing, vol. 30, No. 9, 1999, pp. 623–628.
General Dentistry, Subcutaneous, Orbital, and Mediastinal Emphysema Secondary to to the Use of an Air–Abrasive Device, vol. 28, pp. 31–36, No. 1, 1997.
OperativeDentistry,A Useful Evacuation Aid for Intraoral Air–Abrasive Devices, vol. 28, No. 2, 1997 pp. 105–108.

*Primary Examiner*—Todd E. Manahan
*Attorney, Agent, or Firm*—Ingrid E. Schmidt

[57] ABSTRACT

A containment chamber for use in dental air abrasion comprises a rigid self-supporting chamber having self-supporting walls defining an operating space for performing dental operation. An access opening is provided in one of the walls for introducing a dental tool into the operating space. The chamber further includes an outlet port for coupling the chamber to a suction source and a dam retention member for coupling the chamber to a dental dam.

13 Claims, 6 Drawing Sheets

Fig. 6

CONTAINMENT CHAMBER FOR DENTAL ABRASION

FIELD OF THE INVENTION

This invention relates to an enclosure or chamber which may be used in dentistry to contain debris and to protect doctor, patient and staff, particularly where the patient is being treated using dental air abrasion techniques.

BACKGROUND OF THE INVENTION

Dental air abrasion is a method of abrading a tooth in which an abrasive powder is directed at a tooth in a stream of compressed air and is used instead of or in conjunction with a dental bur for cutting teeth. With air abrasion, dental tissues may be roughened or removed selectively, commonly without the need to "freeze" the patient to anesthetize the affected nerve. Dental air abrasion is finding application in the treatment of many types of lesions, including among other things, the preparation of broken teeth for bonding to restorative resins and composites.

One of the drawbacks of dental air abrasion is the mess created by the abrasive. Some confinement of the compressed air stream surrounding the dental abrasion tool, optionally coupled with suction to evacuate the abrasive powder and debris, is contemplated in the patent literature but has not found wide acceptance commercially. Such devices are described in U.S. Pat. No. 2,637,107; U.S. Pat. No. 5,197,876; U.S. Pat. No. 5,356,292; and U.S. Pat. No. 5,547,376.

A more serious drawback to dental air abrasion is the potentially lethal consequence of emphysema resulting from compressed air penetrating soft tissue in the oral cavity of a patient. It has therefore been recommended that air abrasion techniques should not be practiced without using a dental dam.

Dental dams are usually made of latex rubber or a synthetic rubber like sheet, for example silicone, which is stretched over a frame. The dam is placed inside the patient's mouth to shield the oral cavity and particularly, the patient's digestive tract. A small hole is punched into the sheet to expose any teeth which are being treated and a clamp is used to fasten the sheet around the base of the affected teeth. Where dental abrasion is used to treat the affected teeth, the abrasive which is usually a fine aluminum oxide powder, tends to rebound mostly from the teeth and also from the stretched rubber dam surface into the surrounding air space.

Not only do the abrasive particulates create a fine coating on instruments and furniture, they become airborne and may be inhaled by patients as well as health care professionals. Recent studies have also indicated that blood will contaminate the aerosols produced during air abrasion. Thus while the use of a dental dam is encouraged, there is still a certain reluctance to use rubber dams in conjunction with air abrasion particularly since the wet residue left on a patient's unprotected mouth is easily removed and evacuated using conventional apparatus found in any dentist's office.

There exists a need for a containment chamber which may be used advantageously with air abrasion but also with other dental techniques whereby both the patient and the health care professional are protected so that advantage may be taken of the many benefits which air abrasion has to offer.

SUMMARY OF THE INVENTION

In accordance with this invention, there is provided a rigid self-supporting chamber having an access opening for introducing a dental tool, and at least one outlet port for coupling the chamber to suction means, the chamber having dam retaining means for coupling the chamber to a dental dam.

BRIEF DESCRIPTION OF THE DRAWINGS

A preferred embodiment of the invention exemplifying the claimed features of the invention and other desirable attributes is described below with reference to the accompanying drawings in which:

DETAILED DESCRIPTION OF PREFERRED EMBODIMENT

Figure 1:
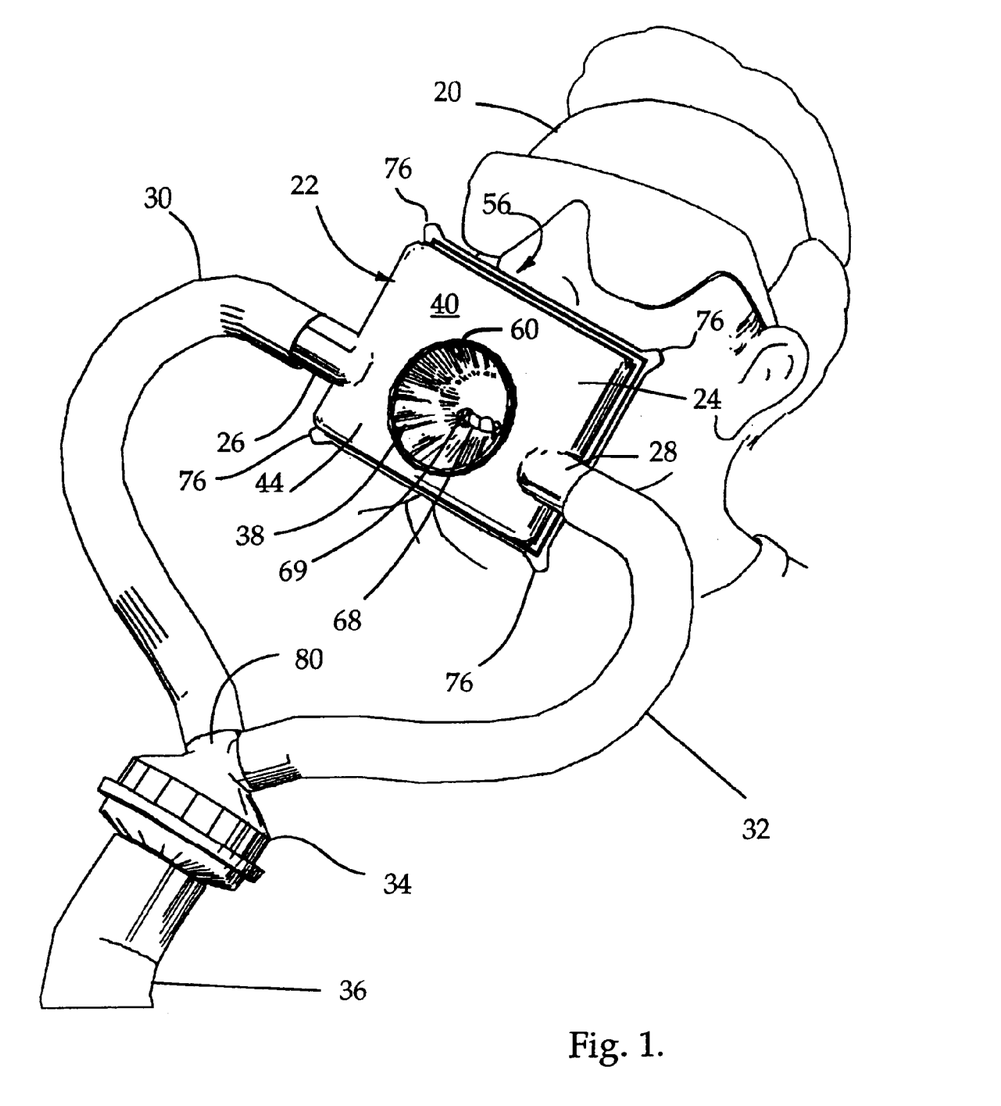
FIG. 1 is a perspective view from the front showing a containment chamber assembly in accordance with the invention in use on a patient.

A containment chamber assembly in accordance with the invention is shown in use on a patient 20 and generally indicated by reference numeral 22 in FIG. 1. The containment chamber assembly 20 comprises a containment chamber 24 having a pair of oppositely directly outlet ports 26, 28 coupled to respective suction hoses 30, 32 each coupled at another end to a common filter assembly 34 disposed between the containment chamber 24 and central suction means (not shown) having a main inlet hose 36.

Figure 3:
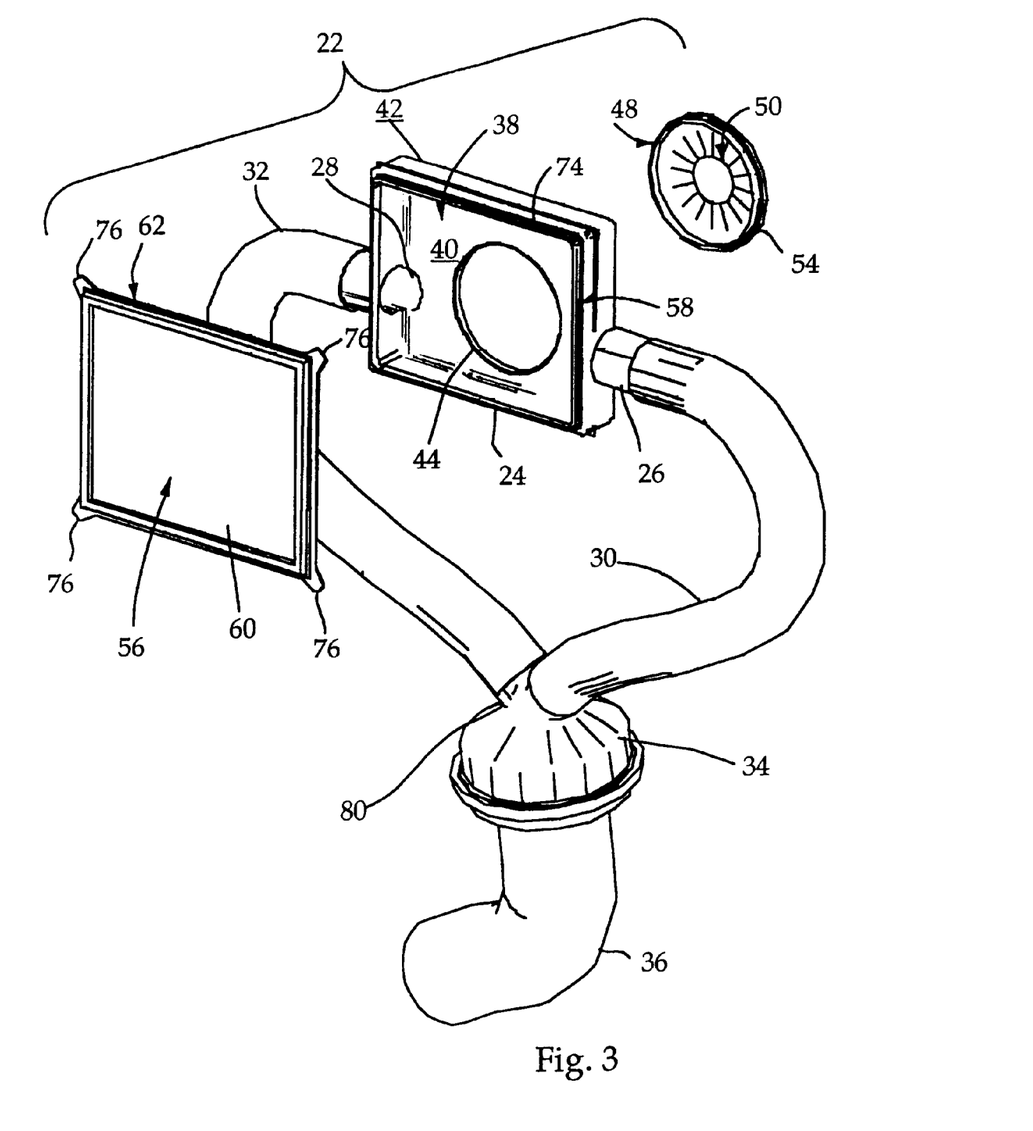
FIG. 3 is an assembly drawing showing the component parts of the containment chamber assembly of FIG. 1.

The component parts of the containment assembly 22 will now be described with particular reference being made to FIG. 3. The containment chamber 24 is preferably made from a transparent synthetic plastic material such as polyethylene tetrahydrate (PET) formed by plastic injection molding into self-supporting walls which define an operating space 38 for performing dental operations. The walls comprise a rectangular front facing surface 40 and a peripheral enclosing surface 42 contiguous with the front facing surface 40 so as to form an open box of shallow depth. The two outlet ports 36, 38 each extend outwardly from the containment chamber 24 from respective portions of the peripheral enclosing surface 42 and comprise small diameter cylindrical portions in fluid communication with the operation space 38.

Figure 2:
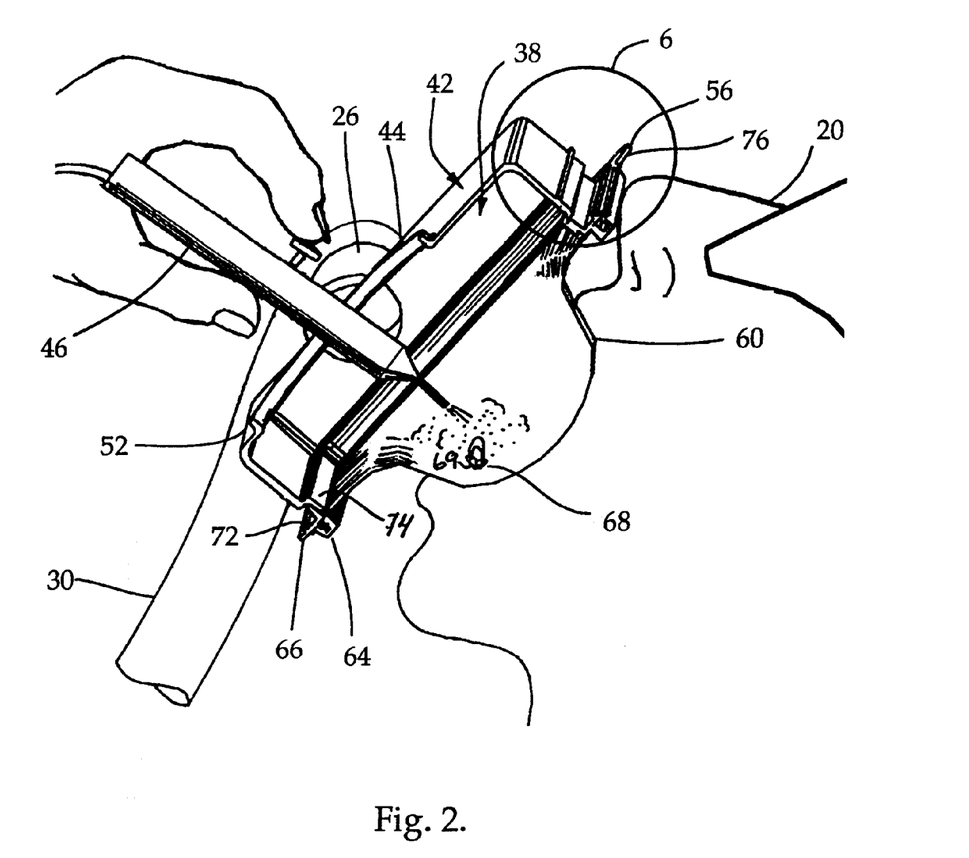
FIG. 2 is a partly sectioned view through the containment chamber of FIG. 1 and showing a dental air abrasion tool introduced into an operating space defined by the containment chamber.

An access opening 44 is formed in the front facing surface 40 and comprises a circular aperture for introducing a dental tool into the operating space 38. An air abrasion dental tool 46 is shown in FIG. 2 received through the access opening 44 and penetrating into the operating space 38. A baffle 48 (FIG. 3) comprising a circular disc having an outside diameter corresponding to the size of the aperture forming the access opening 44 may optionally be used to obstruct the access opening 44 and has a respective aperture 50 through which the dental tool 46 may be introduced.

As can be seen more clearly in FIG. 2, the access opening 44 has a peripheral lip 52 for locating the baffle 48 and which cooperates with a peripheral flange 54 formed in the baffle 48.

The containment chamber assembly 22 is completed by a dam frame assembly generally indicated by reference numeral 56 which is coupled to dam retaining means 58 formed in the peripheral enclosing surface 42 of the containment chamber 24.

Figure 4:
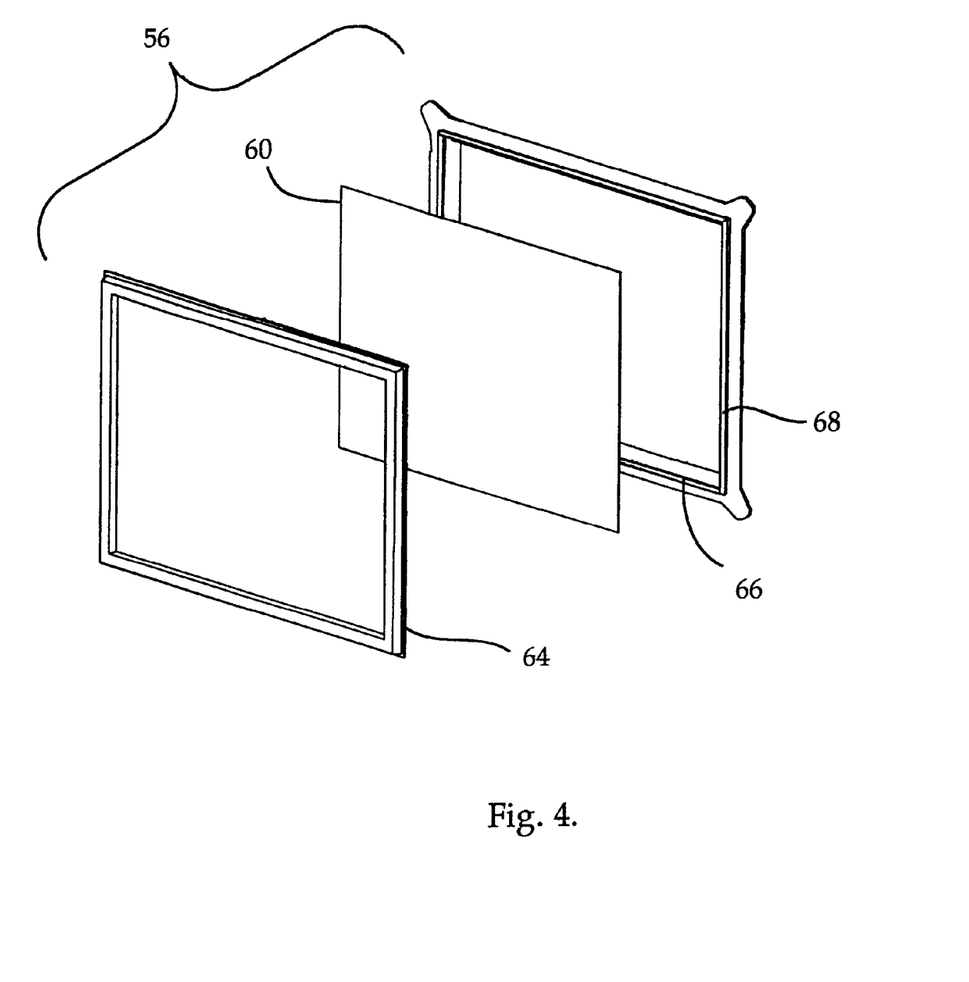
FIG. 4 is an exploded view of a dental dam assembly for use with the containment chamber assembly of FIG. 1.
Figure 6:
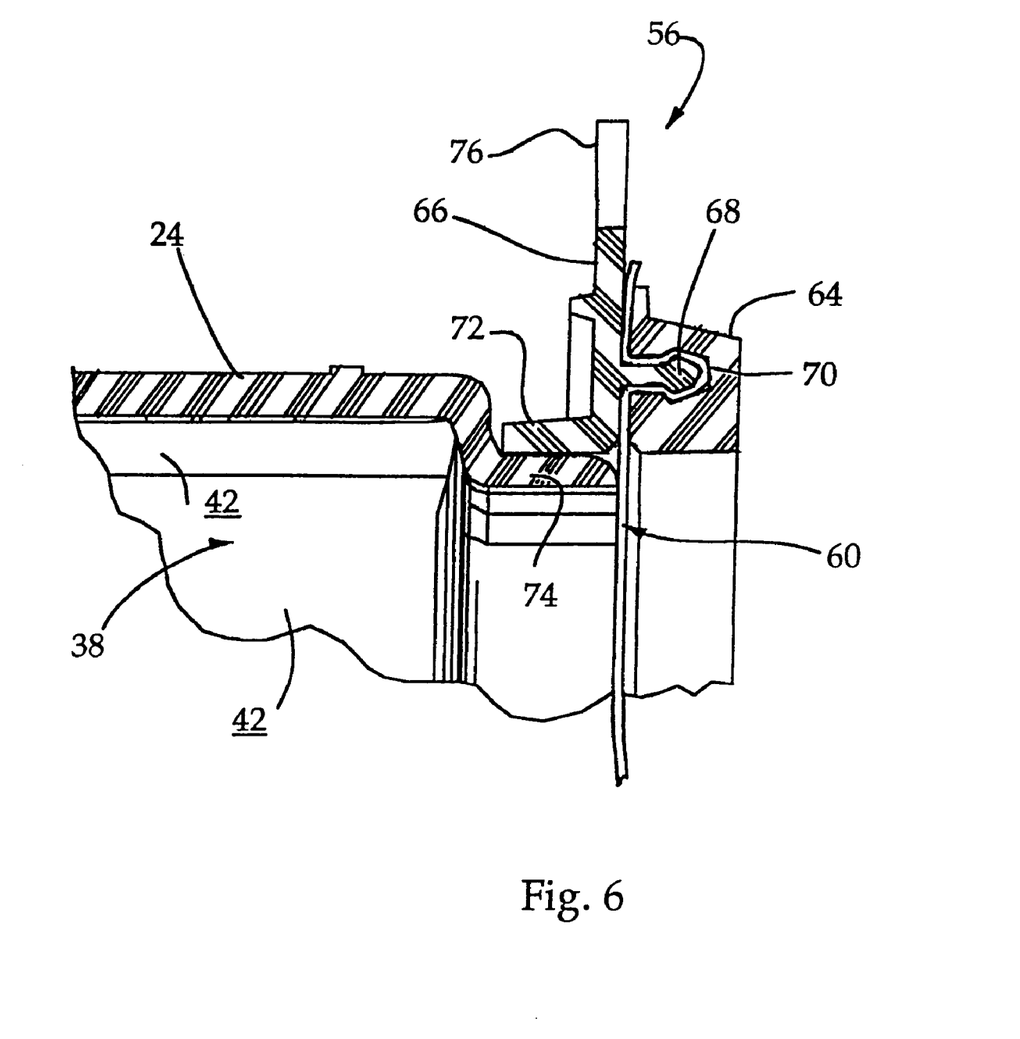
FIG. 6 is drawing to a larger scale and shows means for coupling the dental dam assembly of FIG. 4 to the containment chamber of FIG. 1 in circled area 6 of FIG. 2.

The dam frame assembly 56 is shown in greater detail in FIG. 4 and comprises a dental dam 60 formed from a sheet of latex rubber or silicone as is common in the art, and a peripheral frame 62 comprising a first frame portion 64 and a second frame portion 66, moulded from synthetic plastic material. The dental dam 60 is secured by means of a complementary peripheral ridge 68 formed in second frame portion 66 and engaged by a receiving groove 70 formed in the first frame portion 64 and shown in more detail in FIG. 6.

The second frame portion 66 has a peripheral flange 72 oppositely directed from said ridge 68 and which is adapted to snap fit over a cooperating lip 74 extending rearwardly from the peripheral enclosing surface 42 formed in the containment chamber 24. In this way, the dam 60 is disposed opposite the front facing surface 40 of the containment chamber 24 and thereby defines a back facing surface to close the operating space 38 and isolate the operating space from the oral cavity of the patient 20.

In order to facilitate removal of the dam frame assembly 56 from the containment chamber 24, the second frame portion 66 has a plurality of outwardly extending tabs 76 formed at each corner whereby the frame portion 66 may be flexed so as to release the flange 72 from the lip 74.

In use, a single hole or a number of holes are pierced into the dental dam 60 at selected locations for receiving teeth 68 on which a dental operation is to be performed. The dental dam 60 is secured around the teeth 68 using clamps 69 in conventional fashion. Using the peripheral frame 62, the dental dam 60 is stretched outwardly from the patient's oral cavity and the dam frame assembly 56 is secured to the dam retaining means 58, in this case, peripheral lip 74. The containment chamber 24 is thus positioned outside the patient's face where it rests without 40 causing the patient any appreciable discomfort.

The containment chamber 24 will normally already have suction hoses 30, 32 attached and operatively connected to suction means. A health care professional will have access to the teeth 68 through access opening 44 and may perform any required dental operation, including among others, conventional drilling procedures. This is desirable in that both the patient and the dental health care professionals are isolated from each other by the dam 60 and this affords all parties more protection and peace of mind. The containment chamber 24 is particularly suited for use in association with dental air abrasion techniques which, as described earlier, are messy because of the fine powder abrasive used. It is expected that the fine powder will be contained by the operating space 38 and evacuated through the suction hoses 30, 32 so as to be trapped to a significant degree by the filter assembly 34.

The filter assembly 34 includes an outer casing having a Y junction 80 at one end which couples to the suction hoses 30, 32 and which will include a suitable filter media for trapping the fine abrasive particles used in dental air abrasion.

Perhaps more importantly, the containment chamber 24 will also isolate the oral cavity of the patient 20 so that any air which is emitted from the air abrasion dental tool 46, typically at 100 psi will not have any opportunity to penetrate the soft tissue of the patient and will therefore protect the patient from the dangers associated with air embolisms and emphysema.

For additional protection of the patient 20, a second dental dam may be secured to the affected teeth 68 and its surface, optionally mated to the dam 60 using a suitable sealant, including for example, toothpaste.

Figure 5:
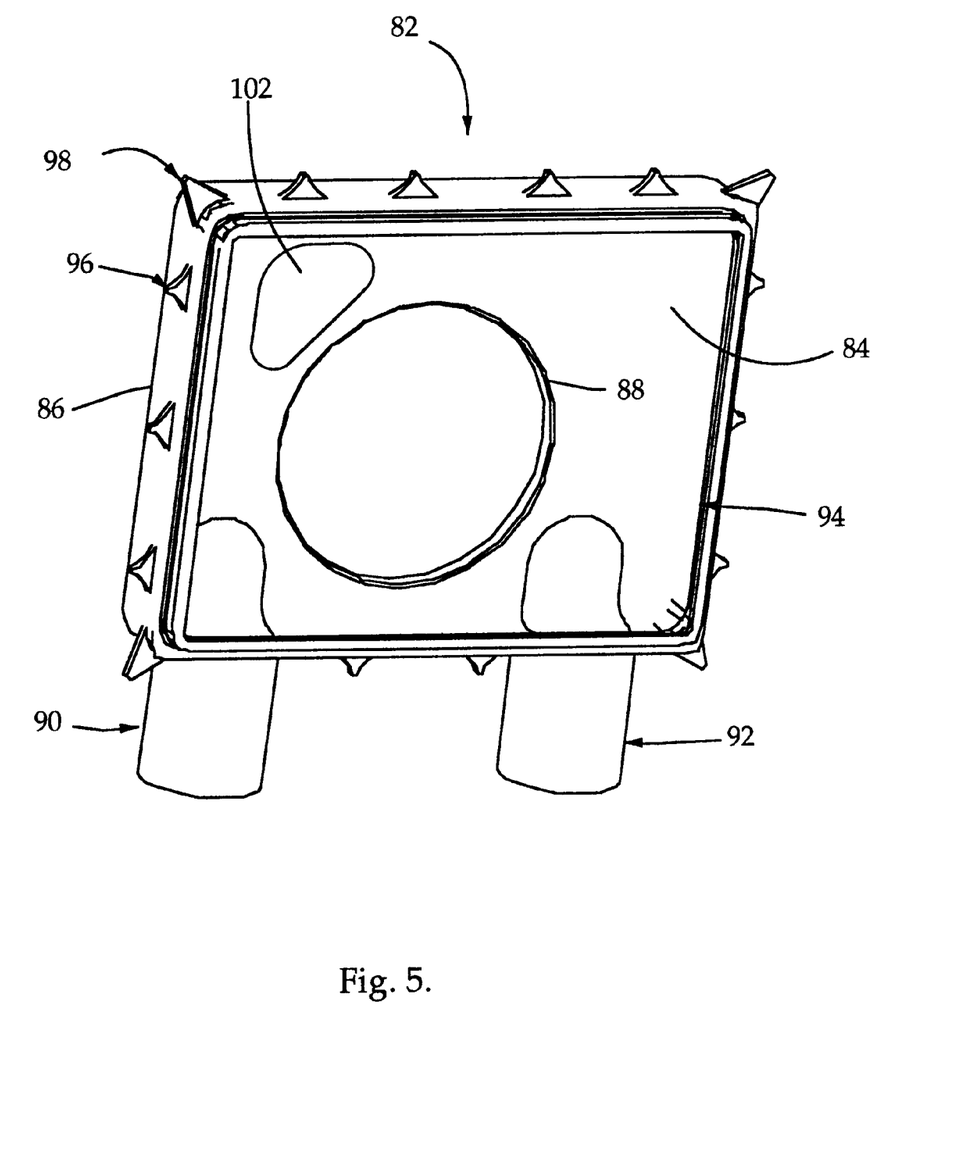
FIG. 5 is a perspective view from the back showing an alternative embodiment of a containment chamber in accordance with the invention.

An alternative embodiment of a containment chamber indicated generally by reference numeral 82 is shown in FIG. 5. Like the containment chamber 24, the containment chamber 82 is formed from walls which define a rectangular front facing surface 84 and a peripheral enclosing surface 86 which extends rearwardly from the front facing surface 84 on four sides thereof. The front facing surface 84 has a circular opening 88 defining an access opening for the containment chamber 82 through which a dental tool may be introduced.

In this embodiment, two spaced outlet ports 90, 92 both extend outwardly from the containment chamber 82 in the same direction on one side from the peripheral enclosing surface 86. In use, the containment chamber 82 is positioned on a patient's mouth so that outlet ports 90, 92 will extend downwardly away from the patient's chin. This configuration of the outlet ports may be advantageous where the containment chamber 82 is used to perform conventional dental operations where rinsing fluids are introduced to remove debris and it is not desired to use an auxiliary suction tool for removal of the fluid. In such a case, a suitable filter assembly will be required which can receive both dry and wet media.

The containment chamber 82 has a rearwardly extending lip 94 formed in the peripheral enclosing surface 86 and which is adapted to receive a dam frame assembly 56 of the kind described above with reference to FIGS. 1 to 4. In addition, the containment chamber 82 has dam retaining means comprising a series of outwardly extending projections 96 which are equally spaced on said peripheral enclosing surface 86 and which have sharp terminations 98 for engaging a dental dam so as to couple the containment chamber 82 to a dental dam with the dental dam disposed opposite to the front facing surface 84. With the projections 96, no special dam frame assembly 56 is required in order to use the containment chamber to its full advantage.

While the containment chamber 82 is made of transparent material, visibility into the operating space 100 defined by the front facing surface 84, peripheral enclosing surfaces 86 and by the associated dam, may be improved by applying a flat magnifying lens 102 to the exterior of the front facing surface 84.

It will be understood that several variations may be made to the above described embodiments of the invention within the scope of the appended claims. In particular, the rectangular shape of the containment chamber shown in the drawings is not a limitation to the structure as the containment chamber may be fabricated to any required shape for the intended application. It will also be understood that the relative size and location of the access opening for introducing a dental tool, may vary, as required, and that while two outlet ports are preferred there may be applications where a single outlet port may be sufficient.

The materials of construction used may also vary considerably and will be selected primarily to ensure the patient's safety while minimizing costs so that the containment chamber assembly may be made entirely disposable and a new containment chamber assembly used for each patient.

It will further be understood that modifications may be made to the suction hoses so as to accommodate valves for regulating the air flow through the hoses and thereby giving the health care professional additional control over the environment in the operating space. Still other such variations will be apparent to those skilled in the art.

We claim:

1. A containment chamber for use in dental air abrasion, the containment chamber having > self-supporting walls defining an operating space for performing dental operations;
> 
> an access opening in at least one said walls for introducing a dental tool into said operating space;
> 
> at least one outlet port in at least one said walls for coupling the chamber to suction means, and
> 
> dam retaining means for coupling the chamber to a dental dam.

2. Containment chamber according to claim 1 which is made from a transparent synthetic plastic material.

3. Containment chamber according to claim 1 in which said walls define a front facing surface, and a peripheral enclosing surface contiguous with said front facing surface, said access opening being formed in said front facing surface, and said at least one outlet port being formed in said peripheral enclosing surface, and said dam retaining means being formed in said peripheral enclosing surface for coupling the chamber to a dental dam disposed opposite to said front facing surface.

4. Containment chamber according to claim 3 in which there are two spaced outlet ports both extending outwardly from the containment chamber in the same direction.

5. Containment chamber according to claim 3 in which there are two oppositely directed outlet ports, each outlet port extending outwardly from the containment chamber respective portions of said peripheral enclosing surface.

6. Containment chamber according to claim 3 in which the dam retaining means comprises a series of outwardly extending projections having sharp terminations for engaging a dental dam.

7. Containment chamber according to claim 3 in which the dam retaining means comprises a peripheral lip for engaging a complementary frame secured to a dental dam.

8. Containment chamber according to claim 1 including a baffle for obstructing said access opening and apertured to receive a dental tool therethrough.

9. Containment chamber according to claim 1 including at least one magnifying lens disposed on said walls.

10. Containment chamber assembly for use in dental air abrasion comprising a containment chamber having > self-supporting walls defining an operating space for performing dental operations;
> 
> an access opening in at least one said walls for introducing a dental tool into said operating space;
> 
> at least one outlet port in at least one said walls for coupling the chamber to suction means,
> 
> dam retaining means for coupling the chamber to a dental dam;
> 
> and suction hoses coupled to said at least one outlet port, said suction hoses having at least one filter disposed therein for filtering air received from said operating space.

11. Containment chamber assembly according to claim 10 having a baffle for obstructing said access opening and apertured to receive a dental tool therethrough.

12. Containment chamber assembly according to claim 10 having a dental dam assembly comprising a dental dam secured to a peripheral frame adapted to engage said dam retaining means.

13. Containment chamber assembly for use in dental air abrasion comprising a containment chamber having self-supporting walls defining a front facing surface and a peripheral enclosing surface contiguous with said front facing surface, > an access opening formed in said front facing surface for introducing a dental tool into said operating space,
> 
> at least one outlet port formed in said peripheral enclosing surface for coupling the chamber to suction means,
> 
> dam retaining means formed in said peripheral enclosing surface for coupling the chamber to a dental dam,
> 
> and a dental dam assembly comprising a dental dam secured to a peripheral frame adapted to engage said dam retaining means, the dam being disposed opposite to said front facing surface, an operating space for performing dental operations being defined by said walls and the dam.

* * * * *

UNITED STATES PATENT AND TRADEMARK OFFICE
CERTIFICATE OF CORRECTION

PATENT NO.   : 6,135,770  
DATED        : October 24, 2000  
INVENTOR(S)  : Bembenek et al.

Page 1 of 1

It is certified that error appears in the above-identified patent and that said Letters Patent is hereby corrected as shown below:

In the drawing:
Replace Fig. 4. We have corrected the numbering by replacing "68" with -- 78 --.
Replace Fig. 6. We have corrected the numbering by replacing "68" with -- 78 --.

Detailed Description of the Preferred Embodiment:

Column 2,
Line 2, paragraph 1, insert -- is -- befor "generally".
Line 5, paragraph 1, replace "directly" with -- directed --.

Column 3,
Line 7 paragraph 2, replace "68" with -- 78 --.
Line 2 paragraph 3, replace "68" with -- 78 --.
Line 8, paragraph 5, insert -- by -- before "peripheral".

Claim 13, column 13,
Line 7, replace "said" with -- an --.
Line 15, replace "an" with -- said --.

Signed and Sealed this

Thirtieth Day of October, 2001

*Attest:*

NICHOLAS P. GODICI

*Attesting Officer*    Acting Director of the United States Patent and Trademark Office

UNITED STATES PATENT AND TRADEMARK OFFICE
CERTIFICATE OF CORRECTION

PATENT NO.    : 6,135,770
DATED         : October 24, 2000
INVENTOR(S)   : Bembenek et al.

It is certified that error appears in the above-identified patent and that said Letters Patent is hereby corrected as shown below:

Drawings,
Replace Fig. 4. We have corrected the numbering by replacing "68" with -- 78 --.
Replace Fig. 6. We have corrected the numbering by replacing "68" with -- 78 --.

Column 2,
Line 2, insert -- is -- before "generally".
Line 5, replace "directly" with -- directed --.

Column 3,
Line 2, replace "68" with -- 78 --.
Line 7, replace "68" with -- 78 --.
Line 8, insert -- by -- before "peripheral".

Column 6,
Line 7, replace "said" with -- an --.
Line 15, replace "an" with -- said --.

Signed and Sealed this

Eighteenth Day of June, 2002

Attest:

Attesting Officer

JAMES E. ROGAN
Director of the United States Patent and Trademark Office

Fig. 4.

Fig. 6